(12) United States Patent  (10) Patent No.: US 7,612,220 B2
DeLine et al.  (45) Date of Patent: Nov. 3, 2009

(54) CARBON DIOXIDE EXTRACTION OF CORN GERM OIL FROM CORN GERM

(75) Inventors: Kenneth E. DeLine, Avon, CO (US); Daniel L. Claycamp, West Frankfort, IL (US); Daniel Fetherston, Cape Girardeau, MO (US); Rodger T. Marentis, Macungie, PA (US)

(73) Assignee: MOR Technology, LLC, Metropolis, IL (US)

( * ) Notice: Subject to any disclaimer, the term of this patent is extended or adjusted under 35 U.S.C. 154(b) by 30 days.

(21) Appl. No.: 11/716,838

(22) Filed: Mar. 12, 2007

(65) Prior Publication Data

US 2008/0045730 A1  Feb. 21, 2008

Related U.S. Application Data

(60) Provisional application No. 60/838,642, filed on Aug. 18, 2006, provisional application No. 60/858,107, filed on Nov. 10, 2006.

(51) Int. Cl.
*C11B 1/00* (2006.01)
(52) U.S. Cl. ............................................ 554/11
(58) Field of Classification Search .............. 554/11
See application file for complete search history.

(56) References Cited

U.S. PATENT DOCUMENTS

| | | | |
|---|---|---|---|
| 4,018,755 A | 4/1977 | Wang | |
| 4,059,604 A | 11/1977 | Kresse | |
| 4,083,836 A | 4/1978 | Anjou et al. | |
| 4,325,882 A | 4/1982 | Reiners | |
| 4,341,713 A | 7/1982 | Stolp et al. | |
| 4,466,923 A | 8/1984 | Friedrich | |
| 4,495,207 A * | 1/1985 | Christianson et al. | 426/312 |
| 4,515,726 A | 5/1985 | Sullivan | |
| 4,576,820 A | 3/1986 | Hussmann | |
| 4,675,133 A | 6/1987 | Eggers et al. | |
| 4,744,926 A | 5/1988 | Rice | |
| 4,859,371 A | 8/1989 | Diosady et al. | |
| 4,898,673 A * | 2/1990 | Rice et al. | 554/12 |
| 4,994,272 A | 2/1991 | Hussmann | |
| 5,120,558 A | 6/1992 | Nguyen et al. | |
| 5,138,075 A | 8/1992 | Ohgaki et al. | |
| 5,252,729 A | 10/1993 | De Crosta et al. | |
| 5,498,384 A | 3/1996 | Volk et al. | |
| 5,680,812 A | 10/1997 | Linsgeseder | |

(Continued)

FOREIGN PATENT DOCUMENTS

CN 1242416 1/2000

(Continued)

OTHER PUBLICATIONS

U.S. Appl. No. 60/838,642, filed Aug. 18, 2006 entitled "Kernel Fractionation Process".

(Continued)

*Primary Examiner*—Deborah D Carr
(74) *Attorney, Agent, or Firm*—Craig Miles; CR Miles, P.C.

(57) ABSTRACT

Supercritical carbon dioxide extraction of corn germ oil from corn germ utilizing extraction conditions adapted to a dry corn fractionation ethanol production process.

13 Claims, 11 Drawing Sheets

U.S. PATENT DOCUMENTS

Figure 1:
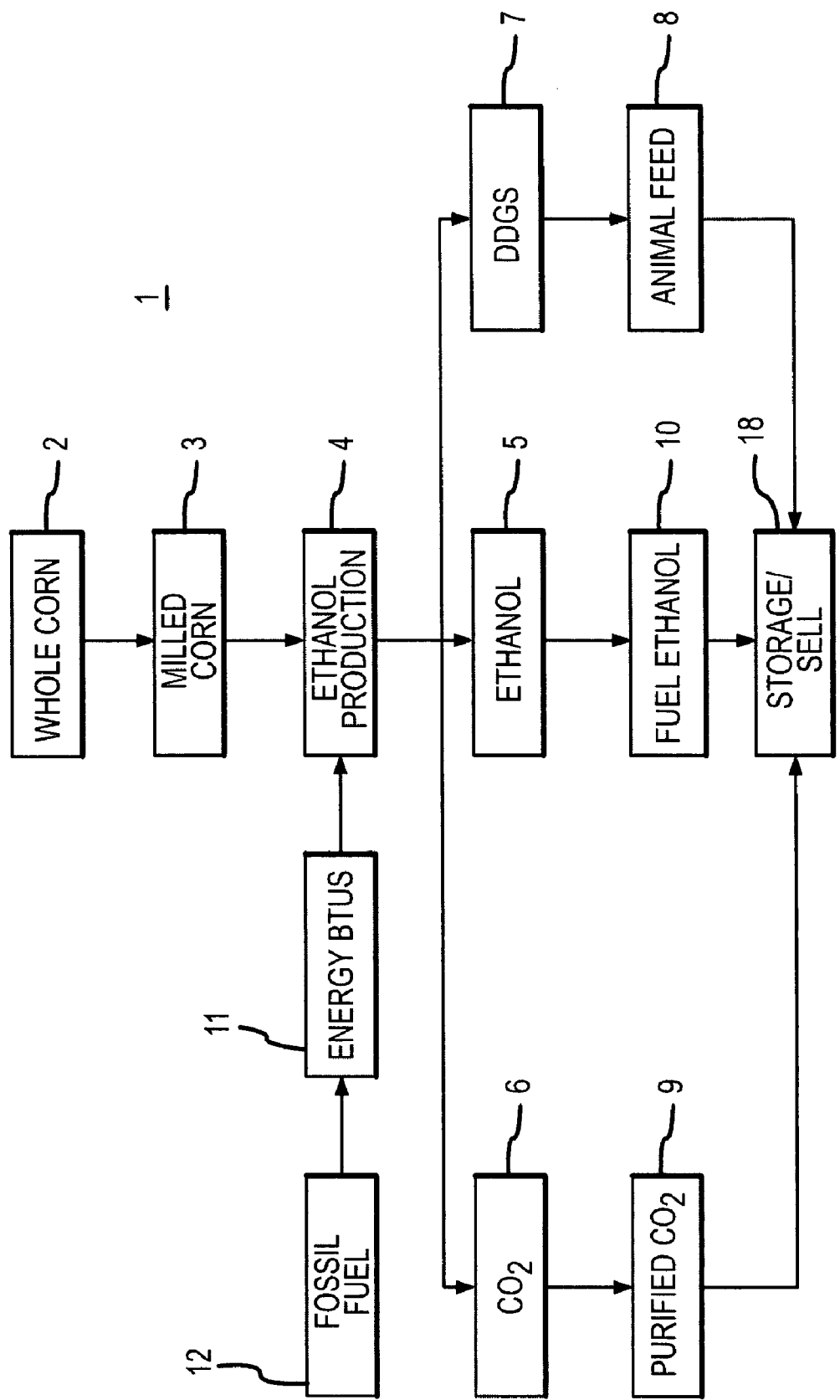

| | | | |
|---|---|---|---|
| 5,685,218 | A | 11/1997 | Kemper |
| 5,759,549 | A | 6/1998 | Hiltunen et al. |
| 5,826,500 | A | 10/1998 | Kemper |
| 5,932,101 | A | 8/1999 | Kanel et al. |
| 5,997,877 | A | 12/1999 | Chang |
| 6,201,142 | B1 | 3/2001 | Maza |
| 6,326,035 | B1 | 12/2001 | Nakatani et al. |
| 6,495,175 | B2 | 12/2002 | Rao et al. |
| 6,504,085 | B1 | 1/2003 | Howard |
| 6,570,030 | B2 | 5/2003 | Goto et al. |
| 6,664,405 | B2 | 12/2003 | Lee |
| 6,814,998 | B1 | 11/2004 | Ozawa et al. |
| 6,936,110 | B2 | 8/2005 | Van Thorre |
| 7,037,548 | B2 | 5/2006 | Ozawa et al. |
| 7,074,449 | B1 | 7/2006 | Holley et al. |
| 7,087,720 | B2 | 8/2006 | Murray et al. |
| 2003/0019736 | A1 | 1/2003 | Garman |
| 2004/0234649 | A1 | 11/2004 | Lewis et al. |
| 2005/0233030 | A1 | 10/2005 | Lewis et al. |
| 2005/0239181 | A1 | 10/2005 | Lewis et al. |
| 2007/0037267 | A1 | 2/2007 | Lewis et al. |

FOREIGN PATENT DOCUMENTS

| | | |
|---|---|---|
| CN | 1522596 | 8/2004 |
| GB | 366516 | 1/1932 |
| GB | 707385 | 4/1954 |
| GB | 1058076 | 2/1967 |
| GB | 1398459 | 6/1975 |
| JP | 6136384 | 5/1994 |
| JP | 6299187 | 10/1994 |
| MX | PA99000033 | 9/2004 |

OTHER PUBLICATIONS

U.S. Appl. No. 60/858,107, filed Nov. 10, 2006 entitled "Power Production Using Grain Fractionation Products".

Kleber, Mark, Mississippi Renewable Energy Conference—Mar. 25-26, 2003, mg engineering Lurgi PSI, Biodesel Capabilities, 2003, pp. 1-28.

Holcomb, Manuel, Harold C. Thompson Jr., Willie M. Cooper and Marvin L. Hopper. SFE Extraction of alfatoxins (B1, B2, G1, and G2) from corn and analysis by HPLC. The Journal of Supercritical Fluids, vol. 9 Issue 2, Jun. 1996, pp. 118-121.

Ronyai, E., B. Simandi, S. Tomoskozi, A. Deak, L. Vigh, and Zs. Weinbrenner. Supercritical fluid extraction of corn germ with carbon dioxide-ethyl alcohol mixture. The Journal of Supercritical Fluids, vol. 14 Issue 1, Oct. 1998, pp. 75- 81.

Otles, Semih. Supercritical Fluids and Its Applications in Food Industry. http://eng.ege.edu.tr/~otles/SupercriticalFluids-ScienceAndTechnology/bolumb/Wc197588f62dd7.htm; 1-4 pages; Mar. 5, 2007.

Taylor, Scott L. Jerry W. King, and Gary R. List. Determination of Oil Content in Oilseeds by Analytical Supercritical Fluid Extraction. JAOCS, vol. 70 Issue 4, Apr. 1993, pp. 437-439.

E. Reverchon, G. Della Porta, D. Gorgoglione. Supercritical $CO_2$ fractionation of jasmine concrete. J. Supercrit. Fluids 8 (1995) 60-65.

E. Reverchon, G. Della Porta. Rose concrete fractionation by supercritical $CO_2$. J. Supercrit. Fluids 9 (1996) 199-204.

R. L. Smith Jr., R.M. Malaluan, W.B. Setianto, H. Inomata, K. Arai. Separation of cashew (*Anacardium occidentale* L.) nut shell liquid with supercritical carbon dioxide. Biores. Technol. 88 (2003) 1-7.

M. A. Rostagno, J.M.A. Araujo, D. Sandi. Supercritical fluid extraction of isoflavones from soybean flour, Food Chem. 78 (2002) 111-117.

L. Sesti Osseo, G. Caputo, I. Gracia, E. Reverchon. Continuous fraction of used frying oil by supercritical CO2. J. Am. Oil Chem. Soc. (JAOCS) 81 (9) (2004) 879-885.

Alberto Bertucco, Francesco Sanmartin and Giuseppe Storti. Simulated moving bed technology for continuous, countercurrent solid-fluid supercritical extraction. The Journal of Supercritical Fluids, vol. 8, Issue 2, Jun. 1995, 138-148.

H. Lee, B.H. Chung and Y. Park. Concentration of tocopherols from soybean sludge by supercritical carbon dioxide. *JAOCS* 68 (1991), p. 571.

G. Brunner, Th. Malchow, K. Stürken and Th. Gottschau. Separation of tocopherols from deodorizer condensates by countercurrent extraction with carbon dioxide. *J. Supercrit. Fluids* 4 (1991), p. 72.

G. Brunner. Gas Extraction—An Introduction to Fundamentals of Supercritical Fluid and the Application to Separation Processes. Springer, Berlin (1994).

J.A. Briones, J.C. Mullins and M.C. Thies. Solvent extraction of fatty acids from natural oils with liquid water at elevated temperatures and pressures. *JAOCS* 67 (1990), p. 852.

P. Bondioli, C. Mariani, A. Lanzani, E. Fedeli and A. Muller. Squalene recovery from olive oil deodorizer distillates. *JAOCS* 70 (1993), p. 763.

O.J. Catchpole and J.C. von Kamp. Extraction of squalene from shark liver oil in a packed column using supercritical $CO_2$. *Ind. Eng. Chem. Res.* 36 (1997), p. 4318.

M.F. Mendes, F.L.P. Pessoa, G.V. Coelho, and A.M.C. Uller. Recovery of the high aggregated compounds present in the deodorizer distillate of vegetable oils using supercritical fluids. JAOCS 34:2, Jun. 2005, pp. 157-162.

D. D. Christianson, J. P. Friedrich, G. R. List, K. Warner, E. B. Bagley, A. C. Stringfellow, G. E. Inglett. Supercritical Fluid Extraction of Dry-Milled Corn Germ with Carbon Dioxide. Journal of Food Science 49 (1), 229-232.

B.M.C. Soares, F.M.C. Gamarra, L.C. Paviani, L.A.G. Goncalves, F.A. Cabral. Solubility of triacyclglycerols in supercritical carbon dioxide. J. Supercrit. Fluids. 2007, 6 total pages.

Ozlem Guclu-Ustundag, Feral Temelli. Correlating the solubility behavior of minor lipid components in supercritical carbon dioxide. J. of Supercritical Fluids 31 (2004) 235-253.

Helena Sovova, Marie Zarevucka, Miroslav Vacek, and Karel Stransky. Solubility of two vegetable oils in supercritical carbon dioxide. J. of Supercritical Fluids 20 (2001) pp. 15-28.

Masturah Markom, Harcharan Singh, and Masitah Hasan. Supercritical $CO_2$ fractionation of crude palm oil. J. of Supercritical Fluids 20 (2001) pp. 45-53.

Reverchon et al., Modeling and simulation of the supercritical $CO_2$ extraction of vegetable oils, Journal of Supercritical Fluids 19, 2001, pp. 161-175.

Lira, C.T., Physical Chemistry of Supercritical Fluids, Supercritical Fluid Extraction and Chromatography Techniques and Applications, American Chemical Society, 1988, pp. 1-25.

\* cited by examiner

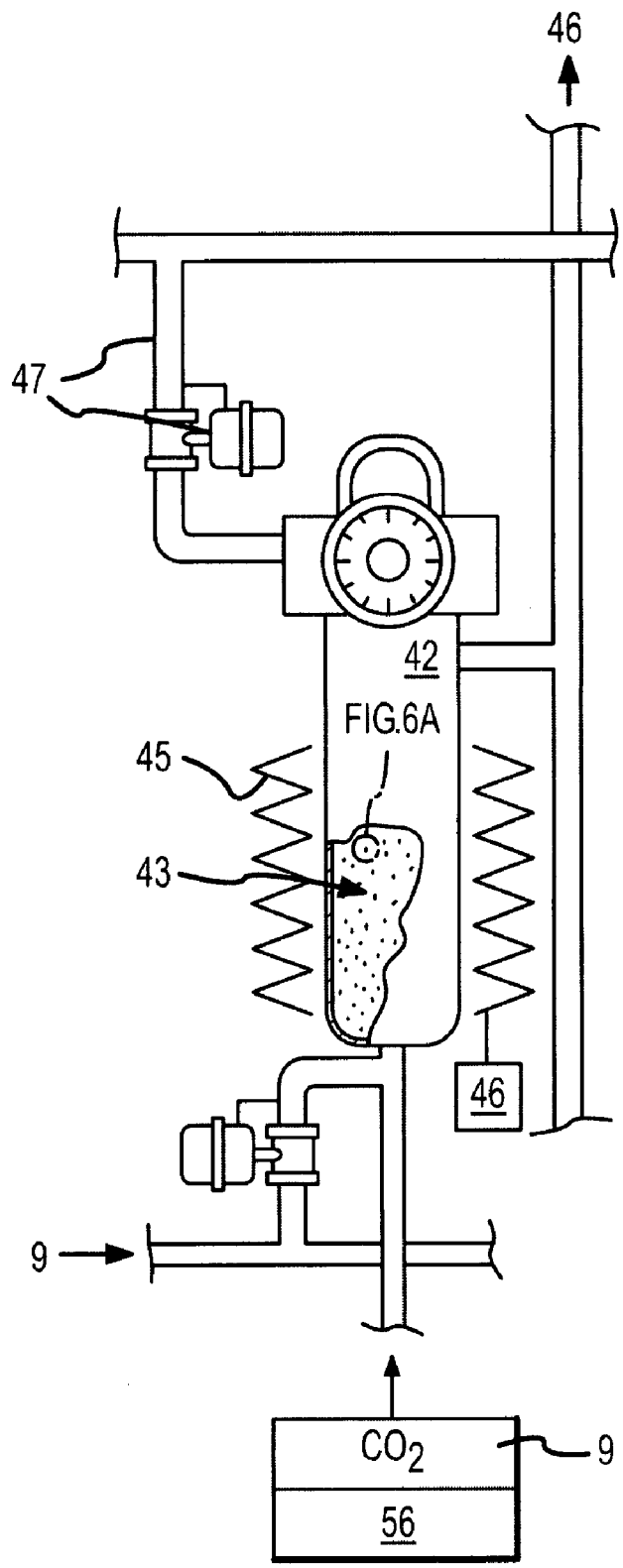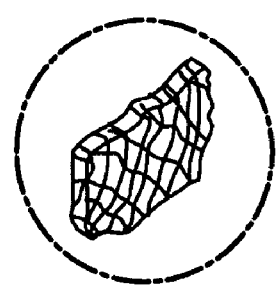
FIG.6A
FIG.6

CARBON DIOXIDE EXTRACTION OF CORN GERM OIL FROM CORN GERM

This U.S. patent application claims the benefit of U.S. Provisional Patent Application No. 60/858,107, filed Nov. 10, 2006 and U.S. Provisional Patent Application No. 60/838, 642, filed Aug. 18, 2006, each hereby incorporated by reference herein.

I. BACKGROUND

Specifically, supercritical carbon dioxide extraction of corn germ oil from corn germ utilizing extraction conditions adapted to a dry corn fractionation ethanol production process. Generally, inventive supercritical carbon dioxide extraction conditions which can be applied to corn germ.

As shown in FIG. 1, conventional ethanol production systems (1) may mill whole corn (2) into a mixture of corn particles (3) (referred to hereinafter as "milled corn") the mixture of particles including corn bran, corn endosperm and corn germ. The milled corn (3) can be transferred to the ethanol production process (4) which includes the conventional steps of fermentation, distillation, and dehydration to generate an amount of ethanol (5). In the fermentation step, the milled corn (3) may be combined with an amount of water and an amount of alpha-amylase (or other enzyme capable of liquefying corn starch) to generate a mash in which the starch of the corn endosperm is liquefied. The mash may be held for a period of time at a temperature of between about 120 degrees Celsius (° C.) and about 150° C. to kill bacteria in the mash. The mash may then be held at a temperature of between about 90° C. and about 100° C. for a duration of time sufficient to achieve a desired level of liquefication of the starch. An amount of gluco-amylase (or other enzyme capable of generating fermentable sugars from the liquefied starch) added to the mash converts the liquefied starch to fermentable sugars, such as dextrose, in a process referred to as saccharification. Yeast can then be added to the mash to convert the sugars to an amount of ethanol (5) and an amount of carbon dioxide (6) (also referred to as "CO2") along with other volatile organics. The amount of carbon dioxide (6) can be placed in a storage unit (18) or sold in the marketplace. For sale into certain markets or for certain applications, the amount of carbon dioxide (6) can be stripped of the other volatile organics and captured as an amount of purified carbon dioxide (9). The fermented mash often referred to as "beer" comprises an amount of ethanol (5) in a concentration of about eight percent to about eighteen percent by weight, other liquids, and non-fermentable solids. The amount of ethanol (5) in the beer can be separated and concentrated to about 190 proof by conventional distillation techniques and dehydrated by application to molecular sieve to produce a dehydrated ethanol of about 200 proof. The about 200 proof ethanol may be combined with up to about five percent denaturant to generate an amount of fuel grade ethanol (10) which can be placed in the storage unit (18) and subsequently sold.

The stillage which remains after distillation of the beer can comprise an amount of liquid typically referred to as "thin stillage" and an amount of remaining solids typically referred to as the "distillers grains". The thin stillage can be separated from the distillers grains (for example by centrifugation). The distillers grains can be dried by evaporation of the remaining thin stillage. The thin stillage can be concentrated by evaporation of water to generate a syrup containing about twenty percent solids to about sixty percent solids (also referred to as "condensed distiller soluble"). The syrup can be recombined with the dried distillers grains to generate an amount of distillers dried grain with solubles (7) ("DDGS"). The DDGS can be sold as animal feed (8).

Even though there is an increasing demand for fuel ethanol (10) worldwide and an increasing amount of research in ethanol production, there remain substantial unresolved problems with respect to conventional ethanol production.

A first substantial problem with the conventional ethanol production process above-described and referring again to FIG. 1 can be that the amount of thermal energy (11) (or energy Btus or Btus) utilized by the conventional ethanol production process (4), including the steps of fermentation, distillation and dehydration, and by-product handling, which results in about a gallon of fuel ethanol (5), and a corresponding amount of DDGS (7) and carbon dioxide (6) may utilize an amount of thermal energy (11) of between about 30,000 and 40,000 British thermal units (hereinafter "Btu"). This amount of thermal energy (11) is typically generated by burning a corresponding amount of fossil fuel (12) such as oil, coal oil, coal or natural gas.

To reduce the amount of fossil fuels (12) utilized to provide the amount of thermal energy (11) required for the ethanol production process (4), an amount of the DDGS (7) may be burned to produce a part of the amount of thermal energy (11) required as described by United States Patent Application No. 2003/0019736A1.

Figure 2:
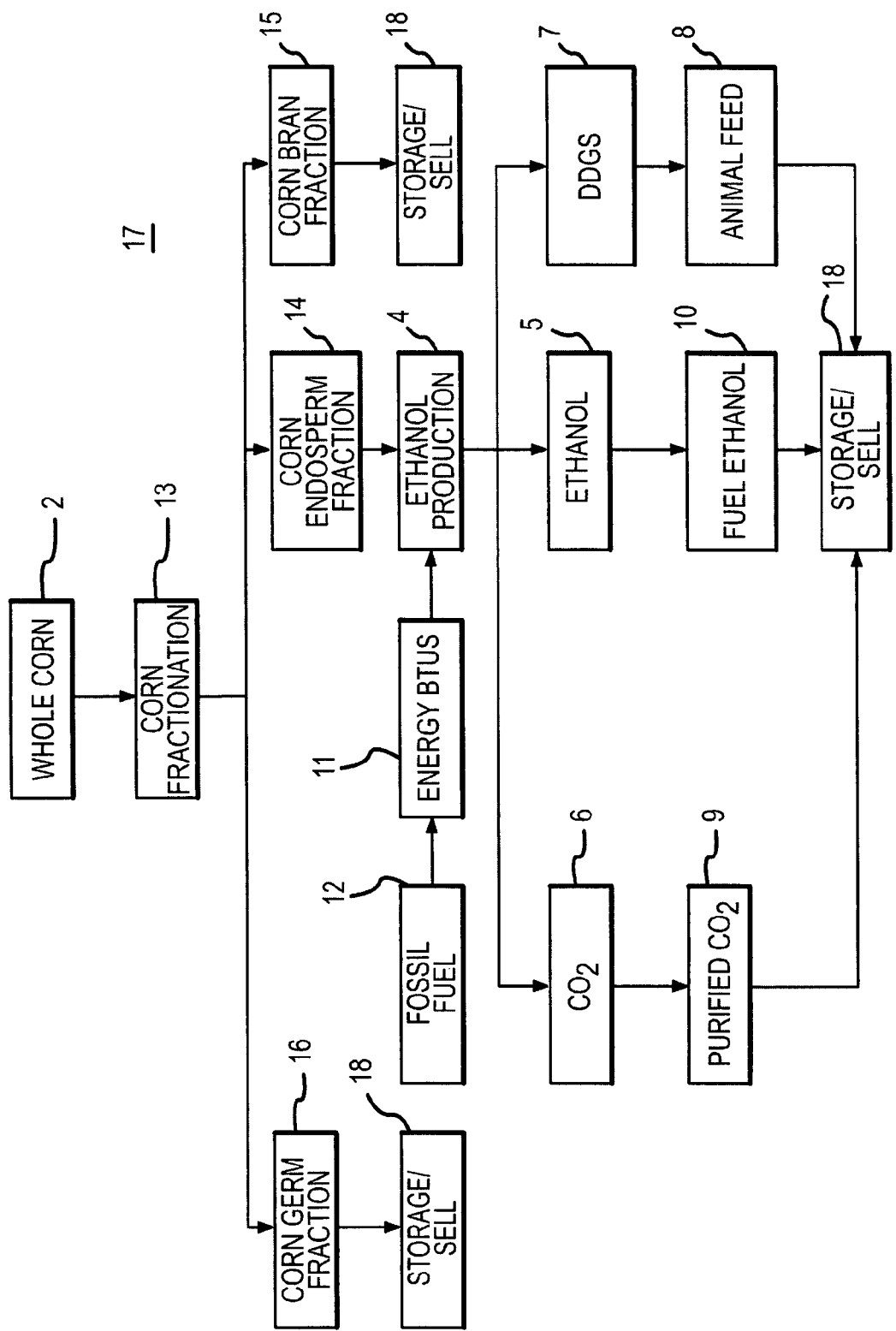

Alternately, referring to FIG. 2, U.S. Patent Application No. 60/838,642, hereby incorporated by reference, inventive dry mill kernel fractionation processes (17) which fracture kernels of grain (13), such as cleaned conditioned corn, and isolate process fractions which include the pericarp (also referred to as "bran"), the germ, and the endosperm can be utilized to reduce the amount of thermal energy (11) required by the ethanol production system (4) or to generate an amount of thermal energy (11) without the use of fossil fuels (12). As shown in FIG. 2, the isolated endosperm fraction (14) can be introduced into the ethanol production process (4) without substantial amounts of the germ fraction (16) or the bran fraction (15). By introducing only the endosperm fraction (14) into the ethanol production process (4) an increased amount of ethanol (5) and fuel ethanol (10) can be generated per unit of fermented material. As the amount of ethanol (5) per unit of fermented material increases, the amount of thermal energy (11) required to produce an amount of ethanol (5) decreases. However, use of the inventive dry mill kernel fractionation processes (17) described also generates an isolated germ fraction (16) and the isolated bran fraction (15) which must be further processed, placed in the storage unit (18), sold, or disposed.

Figure 3:
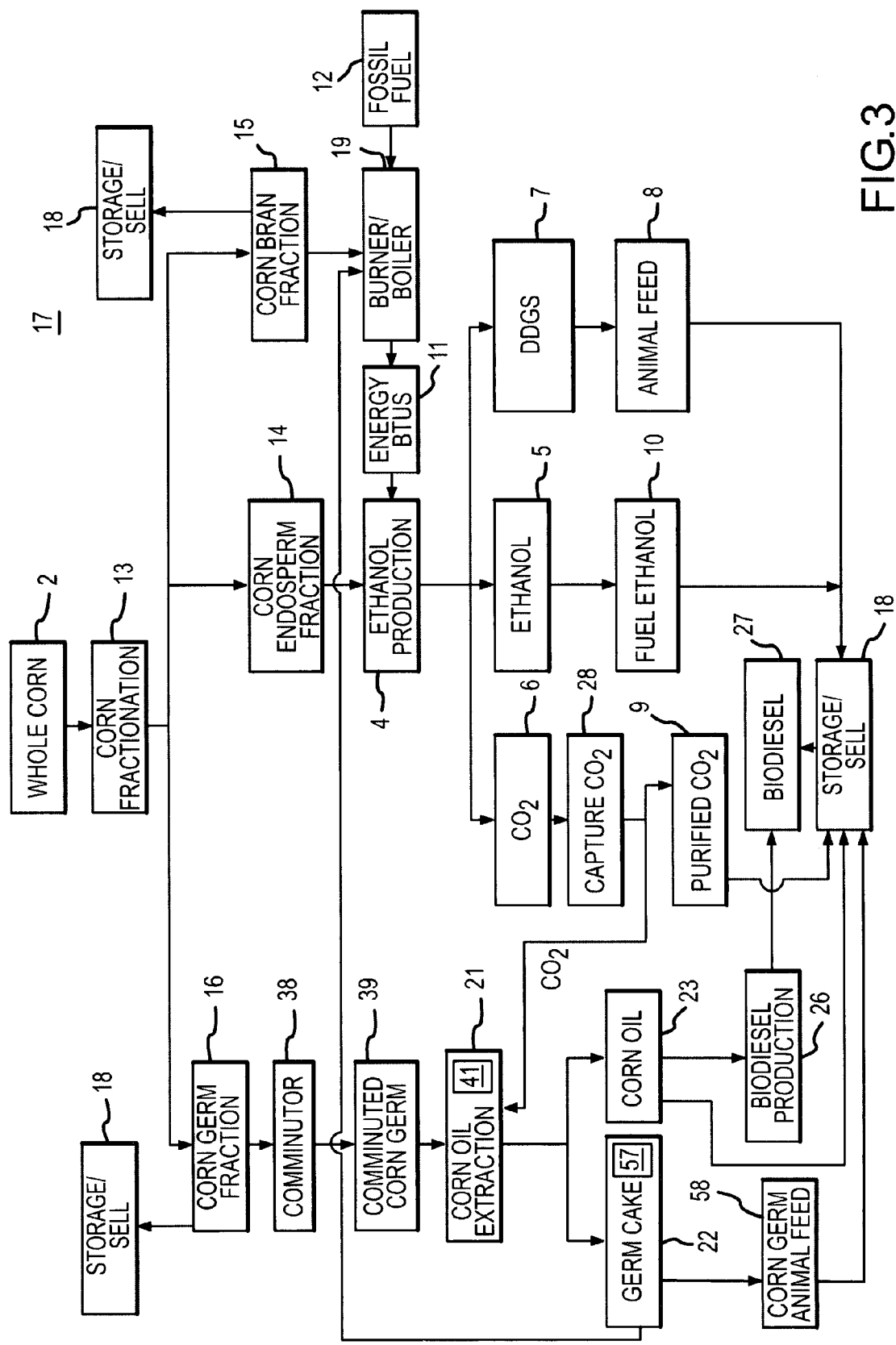
Figure 4:
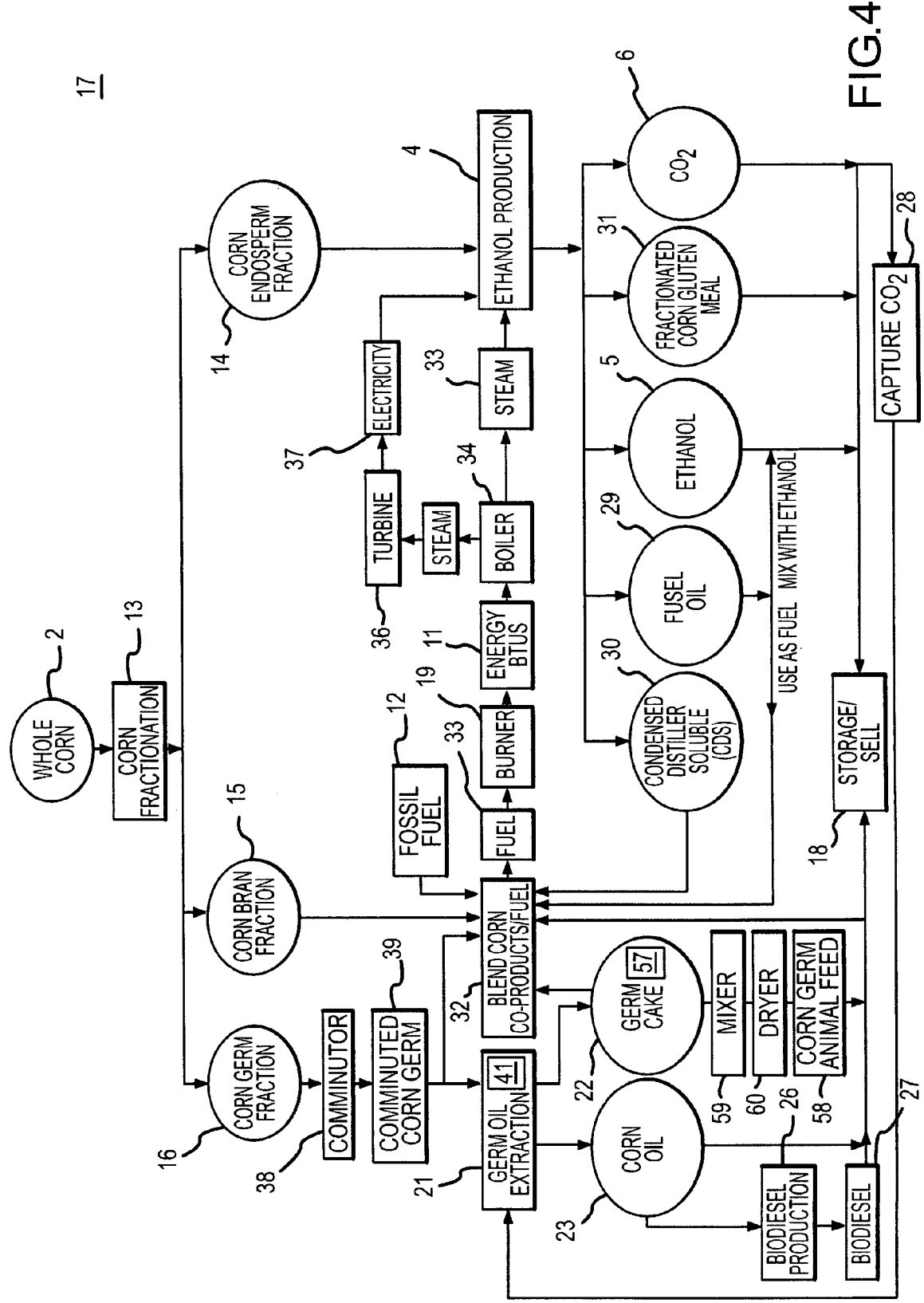

Referring now to FIGS. 3 and 4, various embodiments of the inventive dry mill corn fractionation process (17) as described by U.S. Patent Application No. 60/858,107 and International Patent Cooperation Treaty Patent Application No. PCT/US06/45193, each hereby incorporated by reference, can utilize the isolated germ fraction (16) and the isolated bran fraction (15) (or isolated components thereof whether in whole or in part or separately or in various combinations) to generate an amount of thermal energy (11) to replace in whole or in part the amount of thermal energy (11) conventionally produced by burning fossil fuels (12). With respect to the corn germ fraction (16), extraction of the corn germ fraction (16) with an amount of supercritical carbon dioxide (28) can generate an amount of corn oil (23) which can be placed in the storage unit (18), sold, burned to produce thermal energy (11) or can be converted to biodiesel (27) which can placed in the storage unit (18), sold or burned as a fuel (33) to produce an amount of thermal energy (11) separately or in combination with an amount of any one or more of condensed distiller soluble (30), fusel oil (29), ethanol (5), or fractionated corn gluten meal (31). As to certain embodiments of the invention, the amount of thermal energy (11) can be transferred to a boiler (34) which can produce steam which coupled to a turbine (36) can generate an amount of electricity (37).

A substantial problem with respect to corn germ oil extraction (21) of the corn germ fraction (16) to produce an amount of corn germ oil (23) can be that conventional carbon dioxide extraction methods whether performed with carbon dioxide or with supercritical carbon dioxide utilize extraction conditions which: may not extract (21) a substantial portion of the amount of the corn oil (23) contained in the corn germ fraction (16), or may extract the amount of corn oil (23) contained in the corn germ fraction (15) at a rate which requires greater than about thirty minutes (the term "about" means greater or lesser than the value or range of values stated by 10 percent, but not does not limit any value or range of values to this broader definition and each value or range of values preceded by the term "about" also includes in the alternative the absolute value or range of values stated), or may not extract an amount of corn oil (23) from the corn germ fraction (16) of between about 18 weight percent to about 30 weight percent (such weight percent including any processing of the corn germ to remove a part of the oil prior to extraction with carbon dioxide or supercritical carbon dioxide), or may not extract 90 percent or more of the extractable amount of corn oil (23) in the amount of corn germ fraction (16)), or requires utilization of an amount of supercritical carbon dioxide (28) to the amount of corn germ fraction (16) extracted of greater than about 5 to 1 (wt./wt.) (as a non-limiting example, ratios of 5 to 1 or less may be preferred in certain embodiments of a dry mill corn fractionation process (17) in the context of ethanol production ), or of greater than about 7 to 1 (as a non-limiting example, ratios of 7 to 1 or less may be preferred in other embodiments of the dry mill corn fractionation process (17) in the context of ethanol production), or may greater than about than 12 to 1 (as a non-limiting example, 12 to 1 or less may be preferred in yet other embodiments of the dry mill corn fractionation process (17) in the context of ethanol production).

As such, conventional carbon dioxide extraction methods may be in whole or in part impracticable or incompatible with the process rates or efficiency rates required in the context of a dry mill kernel fractionation ethanol production process (17), or may not be competitive or commercially feasible relative to other conventional methods, or are simply less desirable to extraction conditions which allow between about 18 weight percent to about 30 weight percent of the corn germ fraction (16) (or greater weight percents for corn germ having greater weight percentage extractable corn oil such as about 45 weight percent corn germ oil) to be extracted as corn oil (23) utilizing a ratio of supercritical carbon dioxide (28) to corn germ fraction (16) of not greater than about 12.0 to 1 (wt./wt.), or not greater than 7 to 1, or not greater than 5 to 1, or of greater than 2 to 1 depending on the application. Understandably, the inventive corn germ fraction (16) extraction conditions described herein may confer an advantage in other applications outside of ethanol production systems (17) described herein or incorporated by reference and the invention is not so limited.

Now referring primarily to FIG. 4, another substantial problem with conventional methods of corn germ oil extraction (21) may be that the extracted corn germ fraction (22) (also referred to as "germ cake") may contain an amount of water (25) subsequent to corn oil extraction (21), a portion of which may require evaporation or otherwise removed before the germ cake (22) prior to placement in the storage unit (18) or sold, or which increases the number steps to process the germ cake (22) into a particular germ cake byproduct (27) (such as a germ cake animal feed) or makes the steps to produce a particular germ cake byproduct (27) more costly. As an example, further described below, the condensed distiller soluble (24) above-described can be mixed with the germ cake (22) but the amount of water (25) contained by the germ cake (22) subsequent to mixing which is in excess of about fourteen percent by weight (or in excess of a pre-selected or desired amount of water) must be removed. As such, any reduction in the amount of water (25) contained by the germ cake (22) subsequent to corn oil extraction (21) can reduce the amount of water (25) that must be removed from the germ cake (22) or removed from a mixture of germ cake (22) and condensed distiller soluble (24) to achieve an amount of water in a germ cake animal feed (27) of less than fourteen percent by weight or other water content desirable based upon the application.

The present inventive supercritical carbon dioxide extraction conditions of the corn germ fraction (16) described herein address each of the above-mentioned problems related to conventional corn germ oil extraction from corn germ (16).

II. SUMMARY OF THE INVENTION

Accordingly, a broad object of the invention can be to provide supercritical carbon dioxide extraction of corn germ oil from corn germ utilizing extraction conditions adapted to a dry corn fractionation ethanol production process.

A second broad object of the invention can be to provide inventive supercritical carbon dioxide extraction of corn germ oil from corn germ. The inventive supercritical carbon dioxide extraction conditions as to certain embodiments of the invention can extract greater amounts of corn oil from the same amount of corn germ fraction compared with conventional corn germ extraction conditions. Additionally, the inventive supercritical carbon dioxide extraction conditions can extract the same or greater amounts of corn oil from the corn germ fraction in a lesser duration of time, or can extract an amount of corn oil from an amount of corn germ fraction of between about 18 percent by weight to about 30 percent by weight (or greater weight percentage for corn germ containing for example 45 percent corn oil by wieght) which as to certain embodiments of the invention can be in a lesser duration of time. An additional advantage of utilizing the inventive supercritical carbon dioxide extraction conditions can be a reduction in the amount of supercritical carbon dioxide utilized to extract the same or greater amount of corn oil from the corn germ fraction which as to certain embodiments of the invention can provide a ratio of supercritical carbon dioxide to corn germ fraction extracted of not greater than about 12 to 1 (wt./wt.), or as to certain embodiments of the invention not greater than about 7.0 to 1, or as to certain embodiments of the invention not greater than about 5.0 to 1.0, or as to certain embodiments of the invention between about 2.0-5.0 to 1.0.

A third broad object of the invention can be to provide an extracted corn germ fraction containing an amount of water which can be less than the amount of water contained by conventional corn germ oil extraction processes.

A fourth broad object of the invention can be to provide a corn germ animal feed which includes the germ cake extracted with supercritical carbon dioxide (whether by conventional conditions or the inventive conditions described herein) mixed with an amount of condensed distiller soluble and a method of manufacturing such animal feed which can utilize less thermal energy to bring the mixture to a desired amount of water.

Naturally, further objects of the invention are disclosed throughout other areas of the specification, drawings, and claims.

III. A BRIEF DESCRIPTION OF THE DRAWINGS

FIG. 1 provides a flow diagram of the conventional fuel ethanol production technology.

FIG. 2 provides a flow diagram of a particular embodiment of an inventive fuel ethanol production technology utilizing grain fractionation products.

FIG. 3 provides a flow diagram of a particular embodiment of the inventive fuel ethanol production technology utilizing grain fractionation products.

FIG. 4 provides a flow diagram of a particular embodiment of the inventive fuel ethanol production technology utilizing grain fractionation products.

Figure 5:
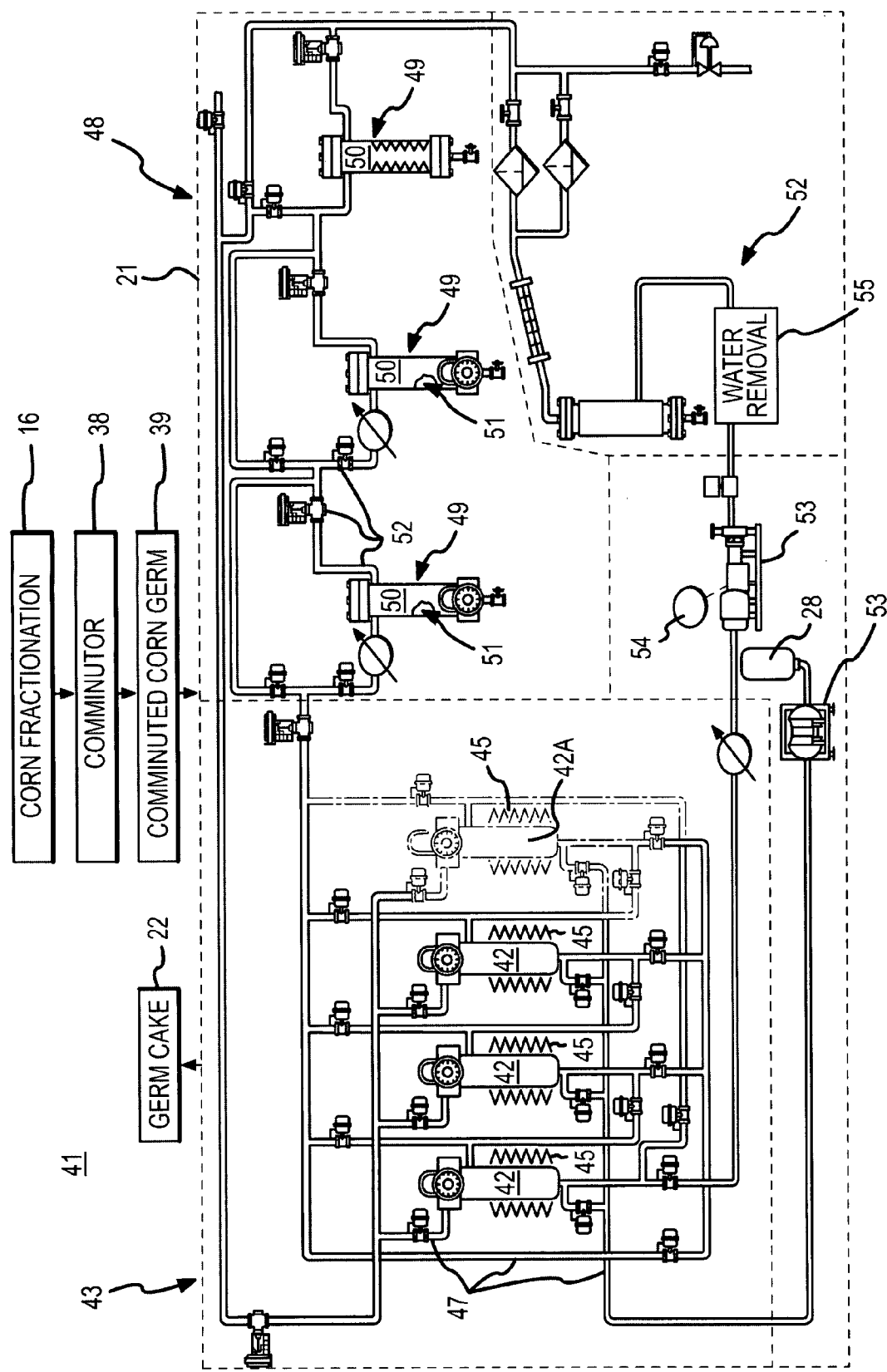

FIG. 5 provides a flow diagram of a particular embodiment of a corn germ extraction system.

FIG. 6 provides an enlarged portion of the flow diagram shown in FIG. 5 further providing a cut away of a part of an extraction vessel showing the corn germ extraction zone containing an amount of corn germ.

FIG. 6A provides an enlargement of one of the plurality of particles included in the amount of corn germ contained in the corn germ extraction zone further illustrating the corn germ matrix.

Figure 7:
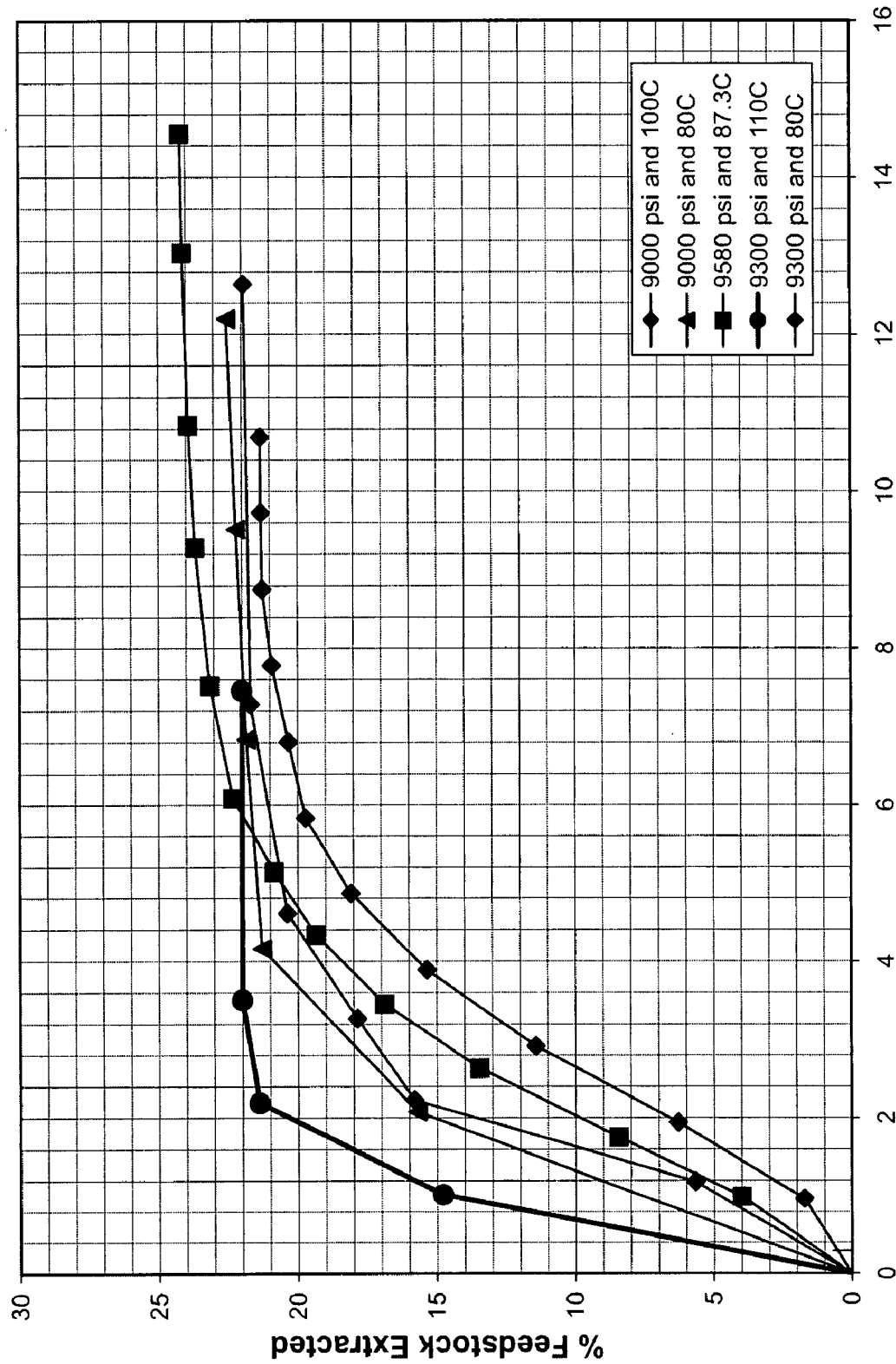

FIG. 7 provides a graph which plots solvent to feed ratio against percent weight of feedstock (weight of corn germ) extracted for certain embodiments of the inventive corn germ extraction conditions.

Figure 8:
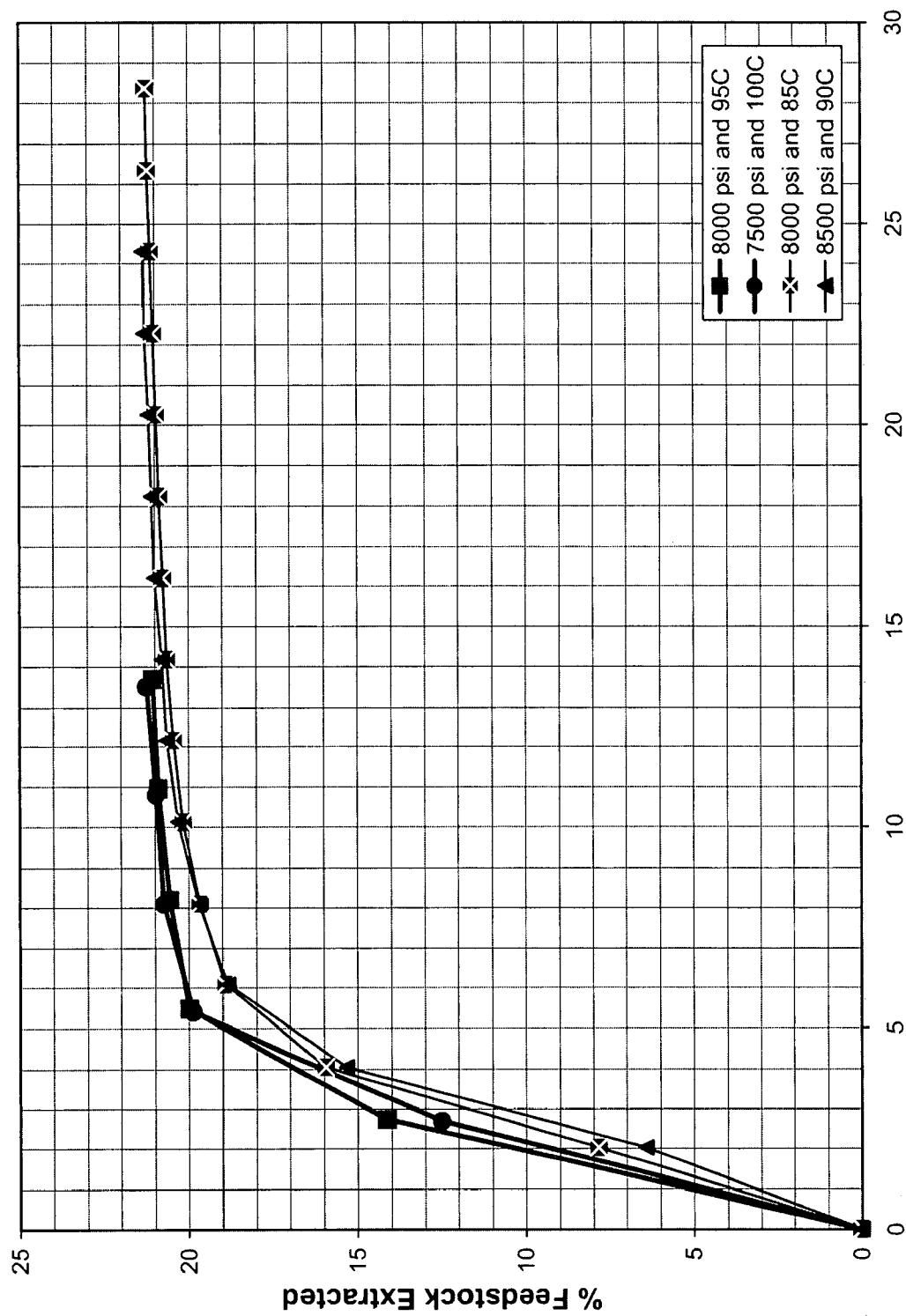

FIG. 8 provides a graph which plots solvent to feed ratio against percent weight of feedstock (weight of corn germ) extracted for certain embodiments of the inventive corn germ extraction conditions.

Figure 9:
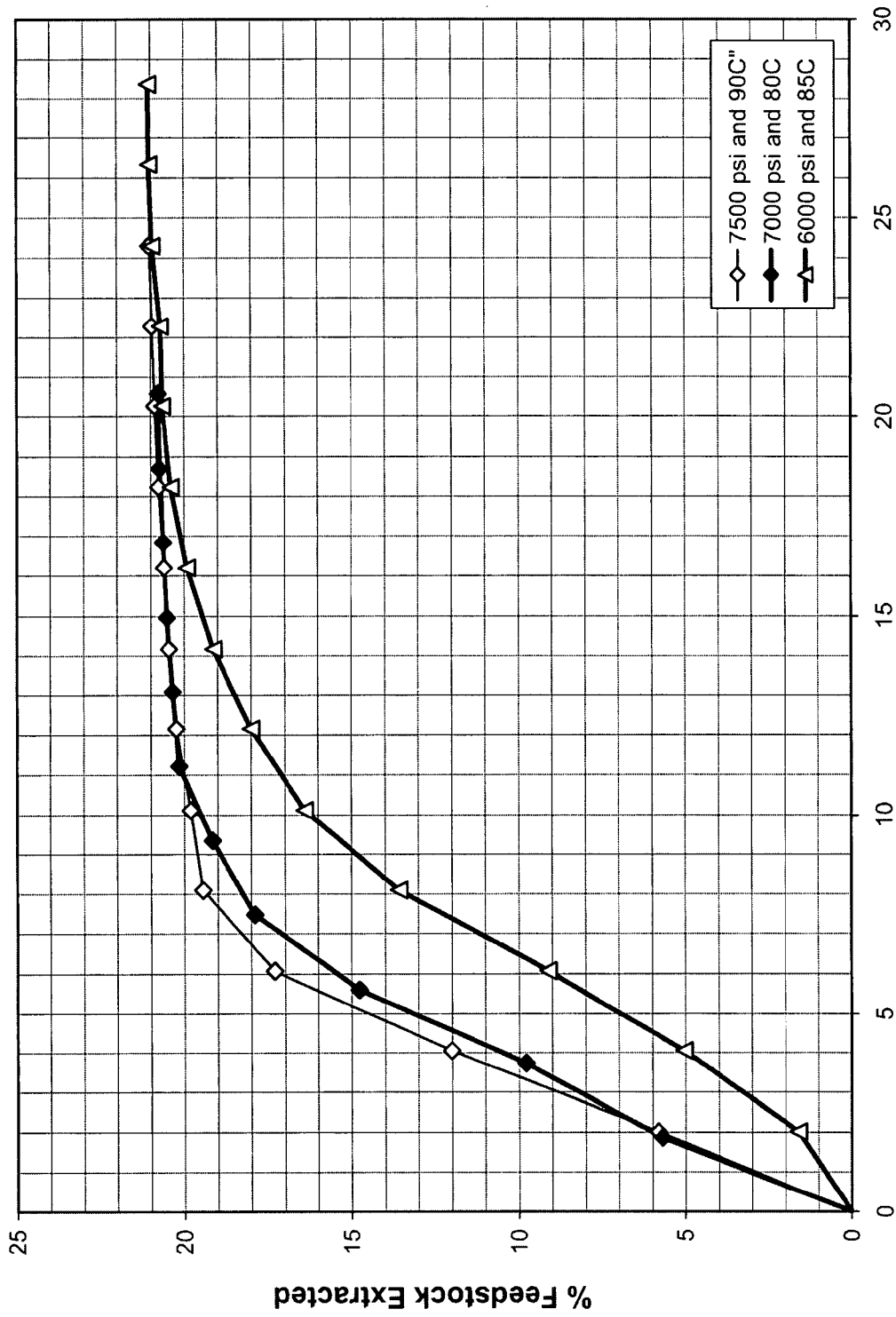

FIG. 9 provides a graph which plots solvent to feed ratio against percent weight of feedstock (weight of corn germ) extracted for certain embodiments of the inventive corn germ extraction conditions.

Figure 10:
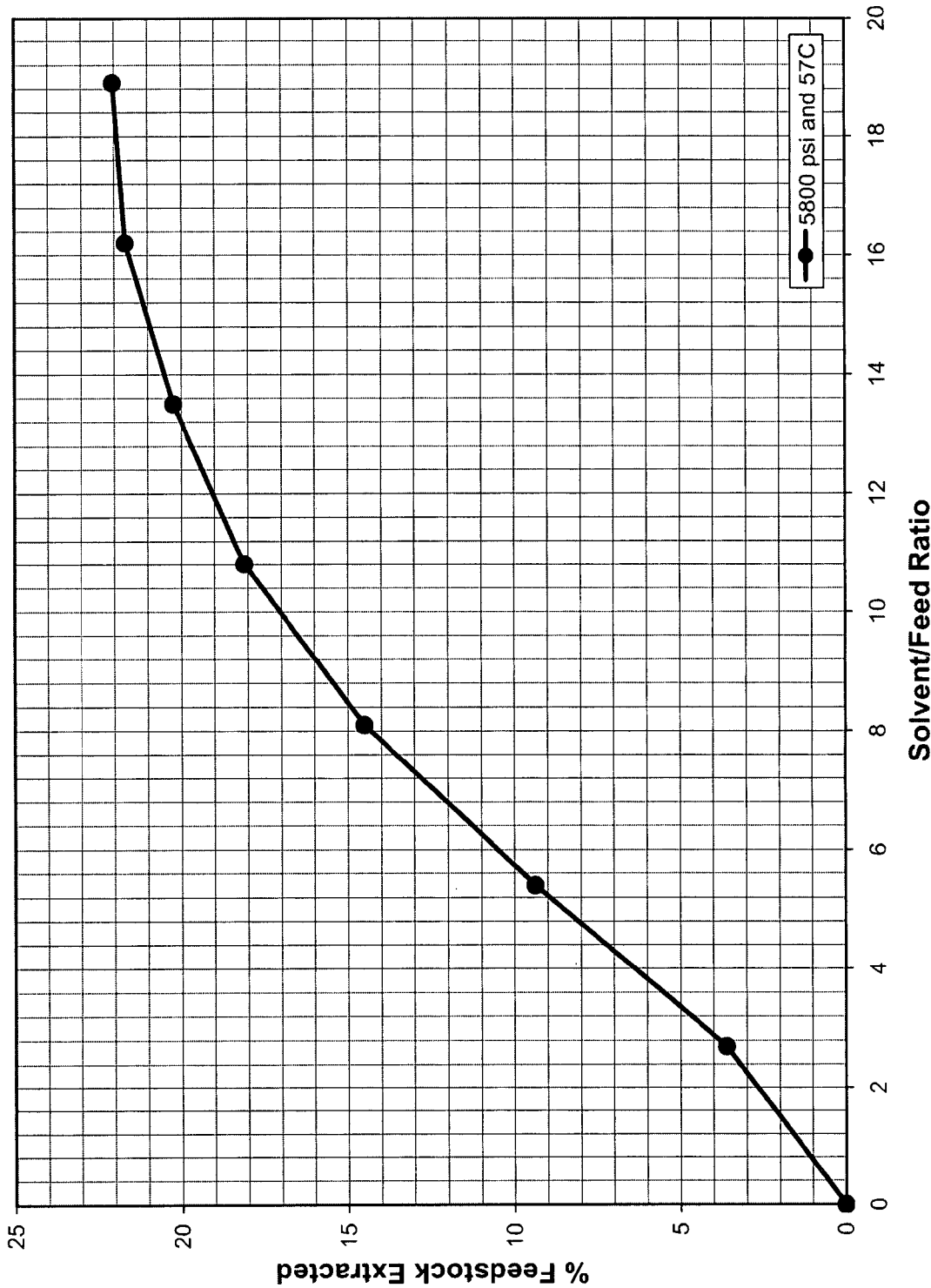

FIG. 10 provides a graph which plots solvent to feed ratio against percent weight of feedstock (weight of corn germ) extracted for certain embodiments of the inventive corn germ extraction conditions.

Figure 11:
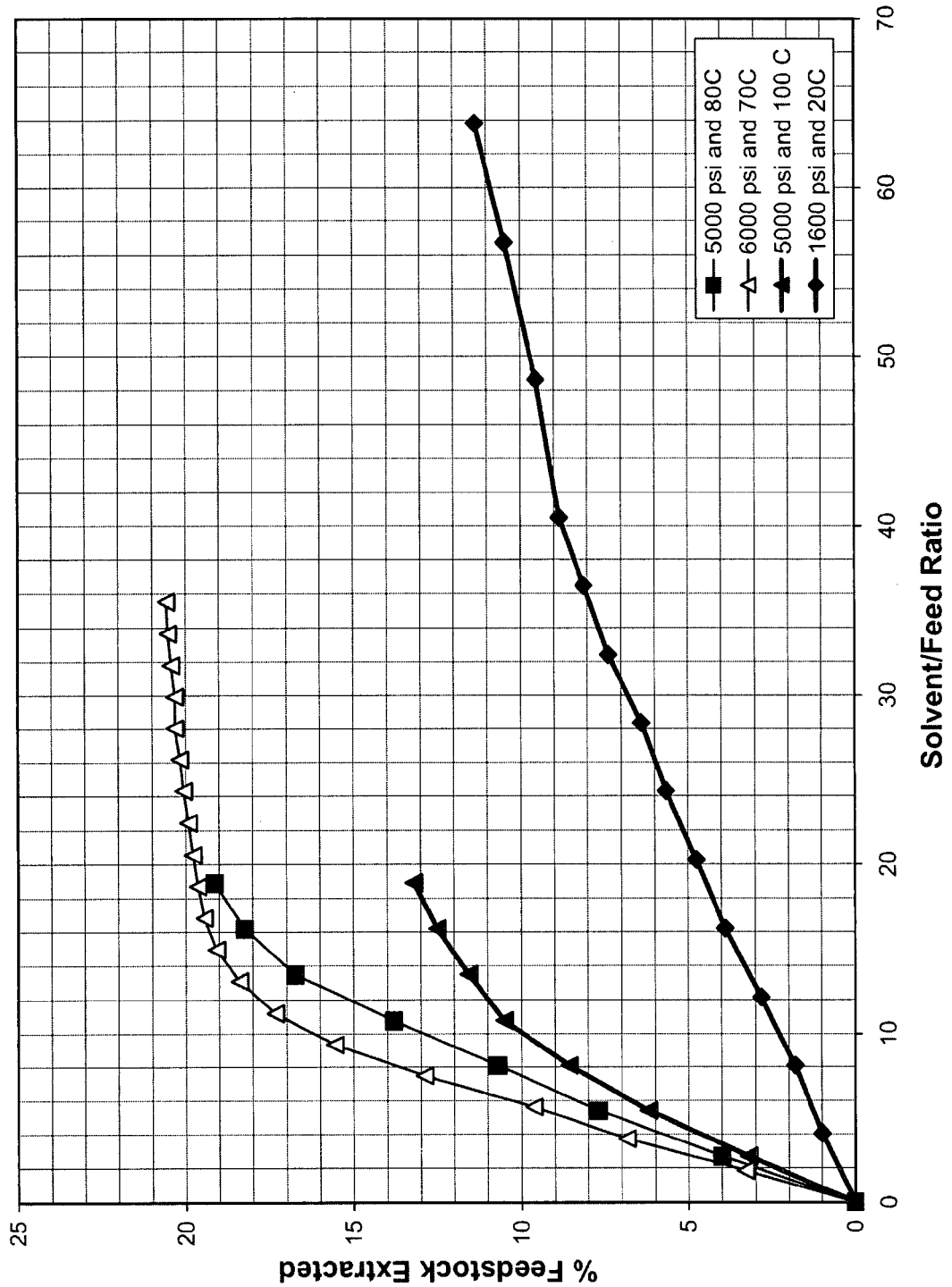

FIG. 11 provides a graph which plots solvent to feed ratio against percent weight of feedstock (weight of corn germ) extracted for certain embodiments of the inventive corn germ extraction conditions.

IV. DETAILED DESCRIPTION OF THE PREFERRED EMBODIMENTS

Specifically, supercritical carbon dioxide extraction of corn germ oil from corn germ utilizing extraction conditions adapted to a dry mill corn fractionation ethanol production process. Generally, inventive supercritical carbon dioxide extraction conditions which can be applied to corn germ to achieve at least one of: greater amounts of corn oil from the same amount of corn germ, generate the same amount of corn oil or greater amounts of corn oil from an amount of corn germ in a lesser duration of time, utilize lesser amounts of supercritical carbon dioxide to generate the same or greater amounts of corn oil from an amount of corn germ.

Now referring primarily to FIGS. 2-4, a corn germ fraction (16) (also referred to in part as "an amount of corn germ") can be generated as above-described or can be generated by any conventional milling process or other corn germ production means. While certain aspects of the inventive supercritical carbon dioxide extraction conditions described herein were adapted for use with the corn fractionation ethanol production systems (17) shown by FIGS. 2-4, the invention is not so limited and the inventive supercritical carbon dioxide extraction conditions can be adapted for use in a wide variety applications which extract an amount of corn germ oil (23) from an amount of corn germ (16).

Now referring primarily to FIGS. 3 and 4, the amount of corn germ (16) can pass through a comminutor (38) to be reduced to a plurality of corn germ particles (39) having a particle configuration (whether by size, range of size, or shape or in various permutations and combinations thereof) suitable for use with the inventive extraction conditions described herein. The particle configuration of the plurality of corn germ particles (39) obtained (whether by sieving, sifting, independent of or in combination with use of a comminutor (38)) allows the amount of supercritical carbon dioxide (9) to fluidicly engage the amount of corn germ (16) in a manner which allows the amount of corn oil (23) (or the extractable portion of corn oil (23)) contained in the amount corn germ (16) to be solubilized and removed from the amount of corn germ (16) at a particular combination of: a temperature, a pressure, a ratio of supercritical carbon dioxide (9) to the amount of corn germ (16) (wt./wt.), and pre-selected duration of time such as a duration of time of between about 10 and about 30 minutes (the "extraction event"). The inventive extraction conditions can be utilized to overcome the unpredictability of a number of factors which affect the extraction event including without limitation differences in the corn germ matrix (40) (see FIG. 6) presented by the amount corn germ (16) which can vary in terms of the porosity, the void volume, the pore configuration or range of pore configurations, resistance to alteration of the corn germ matrix (40) to pressure, resistance to alteration of the corn germ matrix (40) to temperature, the amount of corn germ oil (23) contained by the amount of corn germ (16), the solubility of the corn germ oil (23) or components of the amount of corn germ oil (23) in the amount supercritical carbon dioxide (9), or the like.

Now referring primarily to FIGS. 5 and 6, the plurality of corn germ particles (40) generated from the amount of corn germ (16) must be compatible with a given corn germ oil extraction system (41). A first configuration of the plurality of particles (40) which comprise the amount of corn germ (16) may be compatible with a particular configuration of a corn germ oil extraction system (41) under a first set of extraction conditions and incompatible with the same corn germ oil extraction system (41) under a second set of extraction conditions. For example, under a first set of extraction conditions, the plurality of particles (39) may allow sufficient flow of the amount of supercritical carbon dioxide (9) through one or a plurality of extractor vessels (42) (further described below) while under a second set of extraction conditions, the plurality of particles may restrict flow through one or more of the plurality of extractor vessels (42) such as by reduction of flow of the amount of supercritical carbon dioxide through frits which may be used to retain the plurality of particles (39) in the plurality of extractor vessels (42).

With respect to certain embodiments of the invention utilized with the above-described corn fractionation ethanol production systems (17) (or other corn germ production means), the comminutor (38) can be utilized to reduce the amount of corn germ (16) to the plurality of corn germ particles (39) having a configuration suitable for use with the inventive corn germ oil extraction conditions described herein. The comminutor (38) can operate to reduce the amount of corn germ (16) to the plurality of particles (39) suitable for use with the invention. As to certain non-limiting embodiments of the invention the comminutor (38) can provide a particle configuration which can pass through a 20 mesh screen each opening having a width of opening of about 0.33 inches or about 850 μM but not through a 100 mesh screen each opening having a width of opening of about 0.0060 inches or about 150 μM, or can operate to reduce the amount of corn germ (16) to a plurality of particles (39) which pass through about a 30 mesh sieve each opening having a width of opening of about 0.21 inches or about 540 μM but not through a 100 mesh screen. As too certain embodiments of the invention the comminutor (38) can operate to reduce the amount of corn germ (16) to a plurality of particles (39) which pass through a 20 mesh sieve or a 30 mesh sieve without any limitation as to a lower limit on particle size. A non-limiting example of a comminutor (38) suitable for use with the invention can be a hammermill adjusted to generate the plurality of particles (39) of one or more of the above-described configurations. As but one example, a hammermill available from Bliss Industries, Inc., Ponca City, Okla. can be utilized. With respect to certain embodiments of the invention, one or more sifters, or separators, or air lifts can be utilized separately or in combination with the comminutor (38) to generate the plurality of particles (39) which are not within the defined particle configuration. Each of the trials set out by Example 1 included that portion of an amount corn germ which was ground and passed through a 30 mesh sieve. It is not intended that the above described particle configurations be limiting with respect to the broader range of particle configurations which can be utilized with the inventive extraction conditions further described below.

Now referring primarily to FIGS. 5 and 6, the corn germ oil extraction system (41) can include an extractor assembly (43) such as the cascade extractor shown in the FIG. 5 which provides one or a plurality of extractor vessels (42) each of which define a corn germ extraction zone (43) inside of which the amount of corn germ (16) which can be comminuted to provide a plurality of particles (39) as above-described can be located for fluidic engagement with an amount of supercritical carbon dioxide (9) to perform the extraction event. Each of the extraction vessels (42) can independently perform an extraction event on the amount of corn germ (16) in manner which allows at least one extractor vessel (42A) (shown in broken lines) to come off line for a duration of time after the extraction event sufficient to remove the amount of extracted corn germ (22) and introduce an amount of corn germ (16) for a subsequent extraction event. Each of the plurality of extractor vessels (42) can be coupled to a heat source (45) which generates an amount of heat sufficient to maintain the amount of supercritical carbon dioxide (9) at a temperature of between about 70° C. and about 120° C. during fluidic engagement with the amount of corn germ (16) located inside said corn germ extraction zone. The heat source (45) can be coupled to a temperature adjustment element (46) which can monitor temperature of the amount of supercritical carbon dioxide (9) in the corn germ extraction zone (43) or can monitor other conditions outside of the corn germ extraction zone such as the amount of corn oil (23) solubilized in the amount of supercritical carbon dioxide (9) (the "effluent" (46)) flowing from the corn germ extraction zone (43), or other measure of the efficiency of the extraction event to allow continuous adjustment of the temperature of the amount of supercritical carbon dioxide (9) in the corn germ extraction zone (43) to maintain a preselected temperature, a preselected temperature profile, or a preselected corn germ extraction efficiency profile based on monitoring the effluent (46) from the corn germ extraction zone. The extractor assembly further includes a plurality of conduits and valves (47) configured to allow transfer of the amount of supercritical carbon dioxide (9) into and away from the corn germ extraction zone (43). While a particular example of a cascade extractor is shown in FIG. 5, it is not intended that this configuration of cascade extractor be limiting with respect to the numerous and varied configurations of cascade extractors which could be utilized or made compatible with the inventive supercritical carbon dioxide extraction conditions herein described or utilized with or made compatible with other configurations of extractor assemblies such as a continuous feed extractor which continuously introduces an amount of corn germ (16) into at least one extraction vessel (42) counter current to the continuous introduction of an amount of supercritical carbon dioxide (9).

The corn oil extraction system (41) can further include a carbon dioxide recycle assembly (48) which can include at least one separator (49) having at least one separator vessel (50) which defines at least one corn oil separation zone (51) in which the amount of corn oil (23) extracted from the amount of corn germ (16) can be separated from the amount of supercritical carbon dioxide (9) by establishing one or a plurality of corn oil separation conditions in the at least one corn oil separation zone (51). The at least one separator (49) further includes a plurality of separator conduits and valves (52) configured to allow transfer of the amount of supercritical carbon dioxide (9) into and away from the at least one corn oil separation zone (50 and transfer of the separated amount of corn oil (23) away from the at least one corn oil separation zone (51).

The carbon dioxide recycle assembly (48) can further include a condenser (52) which provides condensing conditions to establish the separated amount of carbon dioxide (9) in a phase compatible with a pressure generator (53) which establishes and maintains the amount of supercritical carbon dioxide at pressure between about 7,000 psi and about 12,000 psi in the corn germ extraction zone (43). The pressure generator (53) can be coupled to a pressure adjustment element (54) which can monitor the pressure of the amount supercritical carbon dioxide (9) in the corn germ extraction zone (43) or can monitor other conditions outside of the corn germ extraction zone (43) such as the amount of corn oil solubilized in the effluent (46), or other measure of the efficiency of the extraction event to allow continuous adjustment of the pressure of the amount of supercritical carbon dioxide (9) in the corn germ extraction zone (43) to establish or maintain a preselected pressure, a preselected pressure profile, or a preselected corn germ extraction efficiency profile based on monitoring the effluent (46) from the corn germ extraction zone (43).

Now referring primarily to FIG. 5 and Table 1 set out below, it can be understood that if the flow rate of the supercritical carbon dioxide (9) in the corn germ extraction zone (43) has a constant velocity (although in practice the velocity can also be varied) then the effects of the alteration of the supercritical carbon dioxide extraction conditions as to a temperature and a pressure can be evaluated as to effect on a ratio of the amount of supercritical carbon dioxide (9) at a given temperature and pressure to the amount of corn germ (16) (wt./wt.) (also referred to as the "solvent to feed ratio") to reach a particular extraction event end point such as an amount of corn oil (23) of about twenty percent of the amount of the corn germ (16) (wt./wt.). For example, if the solvent to feed ratio is about 20 to 1 to obtain extraction of an amount of corn germ oil (23) of twenty percent of the weight of the amount of the corn germ (16) extracted, then for each ton of corn germ oil (23) extracted about twenty tons of supercritical carbon dioxide (9) would be utilized. If the solvent to feed ration is about 2 to 1, then for each ton of corn germ oil (23) extracted two tons of supercritical carbon dioxide (9) would be utilized and so forth. The inventive dry corn fractionation plants above-described as a non-limiting example can process between about 3,000 tons and 5,000 tons of whole corn (2) per day to generate about 250 tons to about 400 tons of corn germ fraction (16). If the corn oil extraction system (41) processes 300 tons of corn germ fraction (16) per day at a solvent to feed ratio of about 20 to 1 then about 6,000 tons of supercritical carbon dioxide (9) would pass through the corn germ extraction zone (43) of the extractor assembly and be recovered by the carbon dioxide recycle assembly (48) per day. However, if the corn oil extraction system (41) processes the same 300 tons of corn germ fraction (16) per day at a solvent to feed ratio of about 2 to 1 then only 600 tons of supercritical carbon dioxide (9) would pass through the corn germ extraction zone (43) of the extractor assembly (43) and be recovered by the carbon dioxide recycle assembly (48) per day.

Even if the configuration of the extractor assembly (43) remains substantially the same regardless of the solvent to feed ratio because the mass of the amount of corn germ (16) extracted remains constant, it can be understood that at least the components of the carbon dioxide recycle assembly (48) would be necessarily scaled upward as solvent to feed ratio increases over the 10 fold range shown in Table 1. As the solvent to feed ratio increases both the capital costs and the cost to operate the corn germ oil extraction system (41) also increase. Corn germ oil extraction systems (41) which adapted to or built to utilize the inventive solvent to feed ratios in the range of about 2 to 1 to about 6.5 to 1 can be extremely economically operate with respect to both capital cost and operating costs while corn oil extraction systems (41) which are adapted to or utilize the inventive solvent to feed ratios in the range of about 7.0 to 1 to about 18.5 to 1 are likely be only marginally economical to operate, and corn oil extraction systems (41) which utilize solvent to feed ratios of greater than 20 to 1 are likely to be impractical to build or uneconomical to operate.

TABLE 1

Effect of Pressure and Temperature on Extraction Efficiency as Represented by Solvent/Feed Ration to Reach 20% of Feedstock wt/wt Extraction.

| Pressure | Temperature (° C.) | Solvent/Feed Ration to Reach 20% of Feedstock wt/wt Extraction |
|---|---|---|
| 9300 | 110 | ~2.0 |
| 9000 | 100 | ~2.5 |
| 9000 | 80 | ~3.5 |
| 9300 | 80 | ~4.5 |
| 9580 | 87.3 | ~5.0 |
| 8000 | 95 | ~5.5 |
| 7500 | 100 | ~5.5 |
| 8000 | 85 | ~6.0 |
| 8500 | 90 | ~6.5 |
| 7500 | 90 | ~7.0 |
| 7000 | 80 | ~8.0 |
| 6000 | 85 | ~10 |
| 5800 | 57 | ~13.5 |
| 5000 | 80 | >20 |
| 6000 | 70 | ~23 |
| 5000 | 100 | >25 |
| 1600 | 20 | >30 |

Now referring primarily to FIG. 7 and Table 1, certain extraction events are plotted to show the solvent to feed ratio as a function of the percent of the weight of the amount of the corn germ (16) extracted for corn germ extraction conditions which result in solvent to feed ratios of less than about 5 to 1 to achieve extraction of an amount of corn oil (23) of about twenty percent of the weight of the amount of corn germ (16) extracted. It is not intended that the examples shown in Table 1 be limiting with respect to the weight percent of the amount of corn oil which can be achieved utilizing the stated solvent to feed ratios, and significantly greater weight percent corn germ oil may be extracted from an amount of corn germ having significantly greater amounts of extractable corn germ oil (23), as a non-limiting example forty five percent extractable corn oil by weight. Similarly, these examples are not intended to preclude applications to an amount of corn germ oil (23) having a part of the extractable corn germ oil (23) removed prior to extraction with an amount of supercritical carbon dioxide in which case the remaining extractable amount of corn germ oil may be less than twenty percent by weight. As such the term "an amount of corn germ" is intended to include any source of corn germ or pre-processed corn germ whether or not a part of the corn germ oil (23) has been prior removed by another process(es) prior to extraction with the invention extraction conditions described herein.

As can be understood from the plots shown, fluidically engaging an amount of supercritical carbon dioxide (9) with an amount of corn germ (16) at a pressure of between about 9,000 psi and about 10,000 psi and at temperatures of between about 80° C. and about 110° C. (even greater pressures of up to 12,000 psi and even greater temperatures of up to about 120° C. can be utilized) can achieve solvent to feed ratios of less than about 5 to 1 and even about 2 to 1 or even less than about 2 to 1 as shown by the examples performed at 9,300 psi and 110° C. (about 1.75 to 1) (see also Examples below). Additionally, dramatic reduction of solvent to feed ratios can be achieved by increasing temperature when the pressure is established at between about 9,000 psi to about 10,000 psi (or even greater pressure up to about 12,000). It is believed that these inventive solvent to feed ratios of less than about 5 to 1, or about 2 to 1, or less that about 2 to 1 and the corn germ extraction conditions utilized to achieve these solvent to feed ratios of between about 9,000 psi and about 10,000 psi and between about 85° C. and about 110° C. (or up to about 12,000 psi and up to about 120° C.) have not been taught prior to the invention.

Now referring primarily to FIG. 8 and Table 1, certain extraction events are plotted to show solvent to feed ratio as a function of the percent of the weight of the amount of the corn germ (16) extracted for corn germ extraction conditions which result in solvent to feed ratios of about 5 to 1 to about 7.0 to 1 to achieve extraction of an amount of corn oil (23) of about twenty percent of the weight of the amount of corn germ (16) extracted. As can be understood from the plots shown, fluidically engaging supercritical carbon dioxide with an amount of corn germ at a pressure of between about 7,500 and about 8,500 psi at temperatures of between about 90° C. and about 100° C. can achieve solvent to feed ratios of between about 5 to 1 to about 7 to 1. It is believed that these advantageous solvent to feed ratios of between 5 to 1 to about and 7 to 1 and the particular corn germ extraction conditions utilized to achieve these solvent to feed ratios of between about 7,500 psi and about 8,500 psi and between about 85° C. and about 100° C. have not been taught prior to the invention.

Now referring primarily FIG. 9 and Table 1, certain extraction events are plotted to show the solvent to feed ratio as a function of the percent of the weight of the amount of the corn germ extracted for corn germ extraction conditions which result in solvent to feed ratios of between about 7.0 to 1 and about 10 to 1 to achieve extraction of an amount of corn oil of about twenty percent of the weight of the amount of corn germ extracted. As can be understood fluidically engaging supercritical carbon dioxide with an amount of corn germ at a pressure of between about 6,000 psi and about 7,500 psi at temperatures of between about 80° C. and about 90° C. can achieve solvent to feed ratios of between about 7 to 1 to about 10 to 1. It is believed that these advantageous solvent to feed ratios of between 7 to 1 to about and 10 to 1 and the particular corn germ extraction conditions utilized to achieve these solvent to feed ratios of between about 6,000 psi and about 7,500 psi and between about 80° C. and about 90° C. have not been taught prior to the invention.

Now referring primarily to FIG. 10 and Table 1, certain extraction events are plotted to show the solvent to feed ratio as a function of the percent of the weight of the amount of the corn germ extracted for corn germ extraction conditions which show that pressure lower than about 6,000 psi and temperatures of about 60° C. result in solvent to feed ratios of greater than about 10 to 1 to achieve extraction of an amount of corn oil of about twenty percent of the weight of the amount of corn germ extracted. Solvent to feed ratios greater than about 10:1 are likely to be impractical or uneconomic in the context of corn fractionation production systems as above-described.

Now referring primarily to FIG. 11 and Table 1, certain extraction events are plotted to show the solvent to feed ratio as a function of the percent of the weight of the amount of the corn germ (16) extracted for corn germ extraction conditions which result in solvent to feed ratios of greater than about 20 to 1 to achieve extraction of an amount of corn oil of about twenty percent of the weight of the amount of corn germ extracted. Solvent to feed ratios greater than about 10:1 are likely to be impractical or uneconomic in the context of corn fractionation production systems as above-described.

Also, as can be seen by the trials run at 5,000 psi that a substantial increase temperature from about 80° C. to 100° C. can actually operate to adversely increase the solvent to feed ratio. This teaches away from the inventive corn germ extraction conditions above described which show substantial reductions in solvent to feed ratio as temperature increases and may account for higher temperatures and pressures not being prior discovered.

Again referring primarily to FIG. 5, the corn oil extraction system (41) can further provide a water removal element (55) which operates to remove an amount of water from the amount of supercritical carbon dioxide (9) prior to fluidic engagement with the amount of corn germ (16) in the corn germ extraction zone (43) to establish an amount of water (56) contained by the amount of supercritical carbon dioxide (9) of about one percent to about seven percent by weight or an amount of water (56) by weight which upon fluidic engagement with the amount of corn germ (16) in the corn germ extraction zone (43) reduces the amount of water (57) contained by the amount of extracted corn germ (22) (see FIGS. 3 and 4) to between about one percent to about fourteen percent by weight.

Again referring primarily to FIG. 4, a corn germ animal feed (58) can be produced by mixing (59) the amount of extracted corn germ (22) having the amount of water (57) reduced to between about one percent to about seven percent by weight with an amount of condensed distiller soluble (30) having a solids content of between about thirty percent to about sixty percent by weight. In one embodiment of the inventive method of producing the corn germ animal feed (58) above described, the amount of condensed distiller soluble (30) mixed (59) with the amount of extracted corn germ (22) increases the amount of water (57) contained by the amount of extracted corn germ to an amount of water (57) by weight which does not exceed about fourteen percent water or does not exceed an amount of water (57) by weight which requires the additional step of drying (60) the animal feed prior to placement in the storage unit (18) or sold. In an alternate embodiment of the inventive method of producing the corn germ animal feed above described, the amount of condensed distiller soluble (30) mixed with the amount of extracted corn germ (22) to introduce the desired amount of solids increases the amount of water (57) contained by the amount of extracted corn germ (22) above fourteen percent by weight or above an amount of water by weight which requires removal of an amount of the water (57) then contained by the amount of extracted corn germ (22). However, this process still confers an advantage because less water needs to be removed (60) than would conventionally be required if the condensed distiller soluble (30) was mixed (59) with an amount of corn germ (16) or with an amount of extracted corn germ (22) which typically contains an amount of water (57) of between about seven percent to about fourteen percent by weight or containing a greater amount of water (57) than between about one percent and about seven percent by weight. By avoiding any removal (60) of the amount of water (57), or by reducing the amount of water (57) to be removed (60), contained by the amount of extracted corn germ (22) subsequent to mixing (59) with the amount of condensed distiller soluble (30), a lesser amount of fuel (33) or thermal energy (11) can be consumed to produce the same amount of corn germ animal feed (58) as above-described. As to those embodiments of the animal feed which require removal of a part of the amount of water (27) contained by the extracted corn germ (22) after mixing (59) with the amount of condensed distiller soluble (30), embodiments of the invention can further include a dryer (60) capable of reducing the amount of water (57) contained by the amount of corn germ (22) mixed (59) with said amount of condensed distillation soluble (30) having the amount of solids in the range of about 20 percent by weight to about 60 percent by weight to between about eight percent by weight to about fourteen percent by weight. Because the amount of water to be removed can be less when the animal feed is prepared by the above-described method, the dryer (60) can be a less expensive type of dryer (60) such as a rotary dryer. A rotary dryer suitable for use with the invention can be obtained for example from FMC Corporation or ICM, Inc.

EXAMPLE 1

A series of trials were conducted to assess the effect of temperature and pressure on the carbon dioxide extraction (21) of corn oil (23) from the corn germ fraction (16) obtained from the corn fractionation process (13).

Trial 1: 100 ml extraction of corn germ: 9200 psi and 90° C. 35.55 g of corn germ feedstock was ground and sieved, and placed in a 100 ml extraction vessel and extracted with pure carbon dioxide at a pressure of 9200 psi and a temperature of 90° C. The flow rate was 4 liters/minute. A total of 8.33 g of yellow corn oil was extracted (23.43% by weight of feedstock). The solvent to feedstock ratio was <8 (S/F<8).

Trial 2: 100 ml extraction of corn germ: 7500 psi and 80° C. 35.55 g of corn germ feedstock was ground and sieved, and placed in a 100 ml extraction vessel and extracted with pure carbon dioxide at a pressure of 7500 psi and a temperature of 80° C. The flow rate was 4 liters/minute. A total of 6.26 g of yellow corn oil was extracted (17.60% by weight of feedstock).

Trial 3: 100 ml extraction of corn germ: 6000 psi and 70° C. 35.55 g of corn germ feedstock was ground and sieved, and placed in a 100 ml extraction vessel and extracted with pure carbon dioxide at a pressure of 6000 psi and a temperature of 70° C. The flow rate was 4 liters/minute. A total of 7.33 g of yellow corn oil was extracted (20.61% by weight of feedstock). Solvent/feed ratio of about 15/1.

Trial 4: 100 ml extraction of corn germ: 5000 psi and 60° C. 35.55 g of corn germ feedstock was ground and sieved, and placed in a 100 ml extraction vessel and extracted with pure carbon dioxide at a pressure of 5000 psi and a temperature of 60° C. The flow rate was 4 liters/minute. A total of 7.38 g of yellow corn oil was extracted (20.75% by weight of feedstock). Solvent/feed ratio of about 25/1.

Trial 5: 100 ml extraction of corn germ: 8000 psi and 85° C. 35.55 g of corn germ feedstock was ground and sieved, and placed in a 100 ml extraction vessel and extracted with pure carbon dioxide at a pressure of 8000 psi and a temperature of 85° C. The flow rate was 4 liters/minute. A total of 7.57 g of yellow corn oil was extracted (21.29% by weight of feedstock). Solvent/feed ratio of about 10/1.

Trial 6: 100 ml extraction of corn germ: 8500 psi and 90° C. 35.55 g of corn germ feedstock was ground arid sieved, and placed in a 100 ml extraction vessel and extracted with pure carbon dioxide at a pressure of 8500 psi and a temperature of 90° C. The flow rate was 4 liters/minute. A total of 7.62 g of yellow corn oil was extracted (21.43% by weight of feedstock). Solvent/feed ratio of about 12/1.

Trial 7: 100 ml extraction of corn germ/7500 psi and 90° C. 35.55 g of corn germ feedstock was ground and sieved, and placed in a 100 ml extraction vessel and extracted with pure carbon dioxide at a pressure of 7500 psi and a temperature of 90° C. The flow rate was 4 liters/minute. A total of 7.50 g of yellow corn oil was extracted (21.09% by weight of feedstock). Solvent/feed ratio of about 12/1.

Trail 8: 100 ml extraction of corn germ: 7000 psi and 80° C. 35.55 g of corn germ feedstock was ground and sieved, and placed in a 100 ml extraction vessel and extracted with pure carbon dioxide at a pressure of 7000 psi and a temperature of 80° C. The flow rate was 4 liters/minute. A total of 7.40 g of yellow corn oil was extracted (20.81% by weight of feedstock). Solvent/feed ratio of about 12/1.

Trial 9: 100 ml extraction of corn germ: 6,000 psi and 85° C. 35.55 g of corn germ feedstock was ground and sieved, and placed in a 100 ml extraction vessel and extracted with pure carbon dioxide at a pressure of 6000 psi and a temperature of 85° C. The flow rate was 4 liters/minute. A total of 7.52 g of yellow corn oil was extracted (21.15% by weight of feedstock). Solvent/feed ratio of about 18/1.

Trial 10: 100 ml extraction of corn germ 1600 psi and 20° C. 35.55 g of corn germ feedstock was ground and sieved, and placed in a 100 ml extraction vessel and extracted with pure carbon dioxide at a pressure of 1600 psi and an ambient temperature of 20° C. The flow rate was 4 liters/minute. A total of 4.22 g of yellow corn oil was extracted (11.87% by weight of feedstock). Solvent/feed ratio is >65/1.

The plots shown in the Figures are the result of these trials or trails similarly performed.

As can be easily understood from the foregoing, the basic concepts of the present invention may be embodied in a variety of ways which includes the best mode of the invention. The invention involves numerous and varied corn germ oil extraction devices and methods of extracting corn oil from corn germ whether derived from conventional corn milling processes, from the kernel fractionation processes incorporated by reference, or otherwise. While certain examples are provided in the context of dry corn fractionation processes, it is not intended that these examples limit the use of the invention to corn germ derived solely from these inventive dry corn fractionation process (17), but rather are intended to be illustrative such that a person of ordinary skill in the art can make and use the invention in the context of the numerous and varied processes that produce an amount of corn germ from which corn germ oil (23) can be extracted.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "extractor" should be understood to encompass disclosure of the act of "extracting"—whether explicitly discussed or not—and, conversely, were there effectively disclosure of the act of "extracting", such a disclosure should be understood to encompass disclosure of a "extractor" and even a "means for extracting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the kernel fractionation devices or systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of extracting an amount of corn oil from an amount of corn germ, comprising the steps of:
   a. locating an amount of corn germ in an extraction vessel;
   b. fluidicly engaging an amount of supercritical carbon dioxide with said amount of corn germ located in said extraction vessel, wherein said amount of supercritical carbon dioxide engaged with said amount of corn germ has a temperature maintained in a range of about 85° C. and about 120° C., and wherein said amount of supercritical carbon dioxide has a pressure maintained in a range of about 8500 psi and about 12,000 psi, and wherein said amount of supercritical carbon dioxide to said amount of corn germ has a ratio in a range of about 2 to about 6 to 1 (wt/wt); and
   c. extracting an amount of corn oil from said amount of corn germ with said amount of supercritical carbon dioxide said amount of corn oil comprising between about 18 weight percent to about 30 weight percent of said amount of corn germ.

2. The method of extracting an amount of corn oil from an amount of corn germ as described in claim 1, further comprising the step of adjusting said temperature and said pressure to achieve said step of extracting said amount of corn oil from said amount of corn germ said amount of corn oil comprising between about 18 weight percent to about 30 weight percent of said amount of corn germ in a duration of time of between about 10 and about 30 minutes.

3. The method of extracting an amount of corn oil from an amount of corn germ as described in claim 2, wherein said supercritical carbon dioxide has a pressure of between about 9,000 psi and about 12,000 psi.

4. The method of extracting an amount of corn oil from an amount of corn germ as described in claim 3, wherein said ratio of said amount of supercritical carbon dioxide to said amount of corn germ has a range of between about 2 to about 5 to 1 (wt/wt).

5. The method of extracting an amount of corn oil from an amount of corn germ as described in claim 4, wherein said temperature maintained in said range is selected from the group consisting of: a temperature range of between about 90° C. and about 120° C., a temperature range of between about 95° C. and about 120° C., a temperature range of between about 100° C. and about 120° C., a temperature range of between about 110° C. and about 120° C., and a temperature range of between about 115° C. and about 120° C., a temperature range of between about 85° C. and about 110° C., a temperature range of between about 90° C. and about 110° C., a temperature range of between about 95° C. and about 110° C., a temperature range of between about 100° C. and about 110° C., a temperature range of between about 105° C. and about 110° C.

6. The method of extracting an amount of corn oil from an amount of corn germ as described in claim 5, wherein said pressure maintained in said range is selected from the group consisting of: a pressure range of between about 9,500 psi and about 12,000 psi, a pressure range of between about 10,000 psi and about 12,000 psi, a pressure range of between about 10,500 psi and about 12,000 psi, a pressure range of between about 11,000 psi and about 12,000 psi, a pressure range of between about 11,500 psi and about 12,000 psi, a pressure range of between about 9,000 psi and about 10,000 psi, and a pressure range of between about 9,500 psi and about 10,000 psi.

7. A method of extracting an amount of corn oil from an amount of corn germ, comprising the steps of:
   a. providing said amount of corn germ;
   b. fluidicly engaging an amount of supercritical carbon dioxide with said amount of corn germ at a ratio of not greater than about 5.0 to 1 (wt/wt);
   c. extracting said amount of corn oil from said amount of corn germ said amount of corn oil comprising between about 20 weight percent to about 30 weight percent of said amount of corn germ.

8. The method of extracting an amount of corn oil from an amount of corn germ as described in claim 7, further comprising the step of maintaining said amount of supercritical carbon dioxide at a temperature of not less than about 85° C. during fluidic engagement with said amount of corn germ.

9. The method of extracting an amount of corn oil from an amount of corn germ as described in claim 8, further comprising the step of maintaining said amount of supercritical carbon dioxide at a pressure of not less than 9,000 psi during fluidic engagement with said amount of corn germ.

10. The method of extracting an amount of corn oil from an amount of corn germ as described in claim 9, further comprising the step of comminuting said amount of corn germ to generate a corn germ particle size fluidicly engaged with said amount of supercritical carbon dioxide in said corn germ extraction zone of less than about 30 mesh.

11. The method of extracting an amount of corn oil from an amount of corn germ as described in claim 10, further comprising the step of reducing an amount of water contained in said amount of supercritical carbon dioxide which fluidicly engages said amount corn germ in said corn germ extraction zone to between about one percent by weight to about seven percent by weight.

12. The method of extracting an amount of corn oil from an amount of corn germ as described in claim 11, further comprising the step of generating an amount of extracted corn germ by fluidic engagement of said amount of corn germ with said amount of supercritical carbon dioxide having said amount of water reduced to between about one percent by weight to about seven percent by weight in said corn germ extraction zone, wherein said amount of extracted corn germ contains an amount of water of between about one percent by weight to about seven percent by weight.

13. The method of extracting an amount of corn oil from an amount of corn germ as described in claim 12, further comprising the steps of:
   a) mixing an amount of distillation soluble having an amount of solids in the range of about 20 percent by weight to about 60 percent by weight with said amount of extracted corn germ containing an amount of water between about one percent by weight to about seven percent by weight sufficient to increase said amount of water contained by said amount of extracted corn germ to greater than fourteen percent by weight; and
   b) drying said extracted corn germ mixed with said amount of distillation soluble having said amount of solids in the range of about 30 percent by weight to about 60 percent by weight to contain an amount of water between about eight percent by weight to about fourteen percent by weight.

* * * * *